United States Patent
Iwasaki et al.

(10) Patent No.: US 7,615,244 B2
(45) Date of Patent: Nov. 10, 2009

(54) **GLYCOPEPTIDE AND PEPTIDE HAVING A *KOKUMI* TASTE IMPARTING FUNCTION, AND METHOD OF IMPARTING THE *KOKUMI* TASTE TO FOODS**

(75) Inventors: Takeshi Iwasaki, Kawasaki (JP);
Naohiro Miyamura, Kawasaki (JP);
Motonaka Kuroda, Kawasaki (JP);
Masanori Kohmura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 645 days.

(21) Appl. No.: 11/248,291

(22) Filed: Oct. 13, 2005

(65) Prior Publication Data

US 2006/0083847 A1    Apr. 20, 2006

Related U.S. Application Data

(63) Continuation of application No. PCT/JP2004/005589, filed on Apr. 20, 2004.

(30) Foreign Application Priority Data

Apr. 25, 2003  (JP)  ............................. 2003-122569
May 15, 2003   (JP)  ............................. 2003-137713

(51) Int. Cl.
*A23L 1/227*   (2006.01)
*C07K 1/12*    (2006.01)
*C07K 5/103*   (2006.01)

(52) U.S. Cl. .................... 426/534; 435/68.1; 435/71.1; 530/322; 530/330; 530/343

(58) Field of Classification Search ........................ None
See application file for complete search history.

(56) References Cited

U.S. PATENT DOCUMENTS 6,730,335 B1 * 5/2004 Indoh et al. .................... 426/18
2002/0058608 A1   5/2002 Cormier et al.

FOREIGN PATENT DOCUMENTS

| JP | 60-9465 | 1/1985 |
| JP | 8-289760 | 11/1996 |
| JP | 10-276709 | 10/1998 |
| JP | 2002-335904 | 11/2002 |
| WO | WO 01/54517 A1 * | 8/2001 |

OTHER PUBLICATIONS

*Food Processing and Ingredients*, "Development of Fish Sauce and its Utilization", 1996, vol. 31, No. 12, pp. 17-20.
Kazuhiro Ikenaka et al, *Journal of Chromatography*, "Analysis of Tissue Glycoprotein Sugar Chains by Two-Dimensional High-Performance Liquid Chromatographic Mapping", 1988, vol. 434, pp. 51-60.
W. E. Gillanders et al, "Class I-restricted cytotoxic T cell recognition of split peptide ligands", *International Immunology*, 1997, vol. 9, No. 1, pp. 81-89.
T. Miyamura, "Koku" o Tsukuridasu Seizo Kakoho', *The Japanese Journal of Taste and Smell Research*, 2002, vol. 9, No. 2, pp. 147-151.
J.W. Slootstra et al, "Structural aspects of antibody-antigen interaction revealed through small random peptide libraries" Molecular Diversity, vol. 1, No. 2, 1995, pp. 87-96, XP008065429.

* cited by examiner

*Primary Examiner*—Jeffrey E Russel
(74) *Attorney, Agent, or Firm*—Oblon, Spivak, McClelland, Maier & Neustadt, L.L.P.

(57) ABSTRACT

Glycopeptides and peptides having the formula:

Val—Asn—His—Thr
 |
 X where X represents a hydrogen atom or a sugar chain, provide a taste improving function, particularly a kokumi taste imparting function. Such glycopeptides and peptides may be used to impart the kokumi taste to foods or seasonings and to improve the kokumi taste in foods with the use of seasonings that contain such glycopeptides and peptides.

12 Claims, No Drawings

GLYCOPEPTIDE AND PEPTIDE HAVING A *KOKUMI* TASTE IMPARTING FUNCTION, AND METHOD OF IMPARTING THE *KOKUMI* TASTE TO FOODS

CROSS REFERENCES TO RELATED APPLICATIONS

This application is a continuation of International Patent Application No. PCT/JP2004/005589, filed on Apr. 20, 2004, and claims priority to Japanese Patent Application No. 2003-122569, filed on Apr. 25, 2003, and Japanese Patent Application No. 2003-137713, filed on May 15, 2003, all of which are incorporated herein by reference in their entireties.

BACKGROUND OF THE INVENTION

1. Field of the Invention

The present invention relates to glycopeptides and peptides which have a taste improving function, particularly a kokumi taste imparting function. The present invention more specifically relates to such glycopeptides and peptides per se, a method for imparting the kokumi taste to foods or seasonings with the use of such a glycopeptide(s) and/or the peptide(s), a method for improving foods in regard to kokumi taste by the use of a seasoning containing such a glycopeptide(s) and/or the peptide(s), and foods or seasonings to which the kokumi taste has been imparted by such a kokumi taste improving method.

2. Discussion of the Background

The term kokumi taste refers to a taste which cannot be expressed by the five basic tastes (sweet taste, salt taste, sour taste, bitter taste, and umami taste), and which is obtainable by enhancing not only the basic tastes but also tastes around, or peripheral to, the basic tastes, such as thickness, spread, continuity, unity, and the like. Heretofore, some methods for imparting a kokumi taste have been reported. Among them, there are known a method in which glutathione is added (see, Japanese Patent No. 1464928), a method in which a heated product of gelatin and tropomyosin is added (see, Japanese Patent Application Laid-open (Kokai) No. Hei 10-276709), a method in which a sulfone group-containing compound is added (see, Japanese Patent Application Laid-open (Kokai) No. Hei 8-289760), and the like.

Further, as a kokumi taste imparting method other than the methods described above, an attempt has been made to impart a kokumi taste by increasing the ratio occupied by peptides in a seasoning (see, "Food Processing and Ingredients", vol 31, No. 12, pp. 17-20 (1996)). This is an attempt to increase the amount of peptides in the whole of a food to impart a kokumi taste to the whole of the food or foods containing the peptides. However, such an attempt failed to provide such a desired effect, because, for example, the titer was low and peptides with bitterness imparted a bitter taste. Further, as described in Japanese Patent Application Laid-open (Kokai) No. 2002-335904, an attempt has been made to provide a seasoning for imparting a kokumi taste obtained by binding sugar and an unspecified peptide according to the Maillard reaction. However, the effect of such seasoning was not so strong, and the seasoning often imparts a negative effect when added to foods, such as impartment of a bitter taste or coloring due to the browned product.

Thus, there remains a need for a method for imparting a kokumi taste to a food. There also remains a need for compounds and seasonings which are effective for imparting a kokumi taste to a food.

SUMMARY OF THE INVENTION

Accordingly, it is one object of the present invention to provide novel methods for imparting a kokumi taste to a food.

It is another object of the present invention to provide novel compounds which are effective for imparting a kokumi taste to a food.

It is another object of the present invention to provide novel seasoning agents which are effective for imparting a kokumi taste to a food.

It is another object of the present invention to provide novel foods in which the kokumi taste has been improved.

In other words, it is an object of the present invention to provide a food material which can be used for wider purposes and has a stronger effect of improving the taste, and which can impart a kokumi taste, that is, enhance the basic tastes and impart thickness, spread, continuity, unity, and the like, associated with the enhancement of the basic tastes.

These and other objects, which will become apparent during the following detailed description, have been achieved by the inventors' discovery that certain novel glycopeptides and peptides have an excellent function of imparting a kokumi taste to foods (including seasonings). Hereinafter, these findings will be described in detail.

In their attempt to complete the present invention, a compound having a kokumi taste imparting function has been to be isolated from a seasoning which has a very strong function of imparting a kokumi taste when added to foods and drinks, in searching compound(s) having a taste improving effect such as impartment of a kokumi taste. Further, since there is a possibility that the amounts of compound(s) to be isolated are very small, judgment according to organoleptic evaluation is also employed.

First, in selecting a starting raw material, the present inventors have selected, as such starting raw material, a seasoning material which had a very strong function of imparting a kokumi taste when added even in a small amount to foods or drinks, and tried to isolate the target compound(s) from such a starting raw material. This is because, in conventional experiments for the purpose of isolating a kokumi taste-imparting compound, the function often becomes vague as fractionation progresses so that fractionation cannot be continued until the compound has been isolated. For these reasons, a seasoning material obtained by decomposing a material containing wheat protein with the use of a Koji-mold, was selected as the starting raw material as being suitable for achieving the object of the present invention. Since this seasoning material exhibits a kokumi taste imparting function when added in an amount of as small as 0.01% to foods or drinks, it is one of the most suitable starting raw materials for achieving the object of the present invention.

As the results of their extensive and intensive investigation, the present inventors have found that a compound having a kokumi taste imparting function in the raw material described above is also contained in a large amount in the fraction having a molecular weight of 1,000 or higher, and that not only peptide which has been conventionally said to be contained therein but also polysaccharide is contained in a large amount.

Therefore, the present inventors have further fractionated the fraction for a molecular weight of 1,000 or higher, of the raw material described above by various procedures to separate-obtain compounds having a kokumi taste imparting function, followed by subjecting the compound to analysis and organoleptic evaluation. As a result, glycopeptides represented by the following sequence formula (I) or (II) were isolated as a compound having a kokumi taste imparting function. There is a report on only the sugar chain moieties of both of the glycopeptides (see. *J. Chromatogr.*, vol. 434, pp. 51-60 (1988)). However, there has been no report that the sugar chain moieties have a flavoring function. Further, peptides which are common to both of the glycopeptides and are represented by the following sequence formula (III), (IV), (V) or (VI) are novel peptides, and there has been no report on the glycopeptide represented by the sequence formula (I) or (II) which is obtained by bonding the peptide to the sugar moiety. These glycopeptides are completely novel glycopeptides.

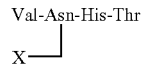

Sequence formula (I)

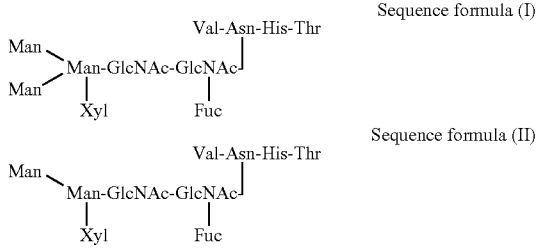

Sequence formula (II)

| Sequence formula (III) | Sequence formula (IV) | Sequence formula (V) | Sequence formula (VI) |
|---|---|---|---|
| Val-Asn-His-Thr | Val-Asn-His | Asn-His-Thr | Asn-His |

In the formulas, Val, Asn, His, and Thr are the same as those in the general formula (b) given later, and GlcNAc is an N-acetyl-glucosamine residue, Fuc is a fucose residue, Man is a mannose residue, and Xyl is a xylose residue. The tetrapeptide sequence and the sugar chain variants appearing above as Sequence formula (I)-(III) are designated as SEQ ID NO: 1.

It has been found, when these glycopeptides and peptides were subjected to organoleptic evaluation, that all the six were substantially tasteless in the form of an aqueous solution, but they exhibited the function of imparting a kokumi taste to food when added even in a very small amount thereto. These findings have led the present invention to completion.

Accordingly, as has been described above, the present invention relates to glycopeptides and peptides which have a taste improving function, particularly a kokumi taste imparting function, specifically to such glycopeptides and peptides per se, a method for imparting the kokumi taste to foods or seasonings with the use of such a glycopeptide(s) and/or the peptide(s), a method for improving foods in kokumi taste with the use of a seasoning containing such a glycopeptide(s) and/or the peptide(s), and foods or seasonings to which the kokumi taste has been imparted by such a kokumi taste improving method.

In this connection, these glycopeptides and peptides are collectively represented by the following general formula (a), and out of these, those represented by the following general formula (b) are particularly excellent in taste improving function.

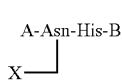

General formula (a)

-continued

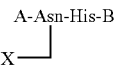

General formula (b)

wherein Asn and His represent an asparagine residue and a histidine residue, respectively, X represents a hydrogen atom or a sugar chain, and A and B each independently represent a hydrogen atom or an amino acid residue.

The tetrapeptide sequence of general formula (b) and the sugar chain variants thereof are designated as SEQ ID NO: 1.

DETAILED DESCRIPTION OF THE PREFERRED EMBODIMENTS

Hereinafter, the present invention will be described in detail.

First, the present invention relates to glycopeptides and peptides which are represented by the following general formula (a), and specific examples thereof include those represented by the sequence formula (I) (SEQ ID NO: 1), (II) (SEQ ID NO: 1), (III) (SEQ ID NO: 1), (IV), (V), or (VI).

A-Asn-His-B
X—⌐

General formula (a)

wherein Asn and His represent an asparagine residue and a histidine residue, respectively, and X represents a hydrogen atom or a sugar chain, and A and B each represent independently a hydrogen atom or an amino acid residue. As described above, these glycopeptides and peptides have a feature in that they have no taste to be specially mentioned in the form of an aqueous solution, but have a taste improving function such as imparting a kokumi taste when added to food even at a concentration of 1 ppb with respect to the food.

In the present invention, the glycopeptide is one in which one or more sugars are bonded to the asparagine which is one of the amino acids constituting the peptide moiety, and the kind of sugar constituting the sugar chain is not particularly limited. The peptide per se of the present invention represented by the sequence formula (III) (SEQ ID NO: 1), (IV), (V), or (VI) has a taste improving effect such as impartment of a kokumi taste, and the like, but the peptide has a feature in that the kokumi taste imparting function thereof is enhanced when the peptide is bonded to a sugar to form a glycopeptide.

The glycopeptides and peptides having the kokumi taste imparting function, of the present invention, should have at least a dipeptide structure of Asn-His in their structure, and a tripeptide and a tetrapeptide are in this order increased in taste enhancing capability.

Although the glycopeptides and the peptides of the present invention can be synthesized, they can be usually obtained from a hydrolyzate which has been obtained by enzymatically hydrolyzing a raw material containing protein.

Such a raw material containing protein is not particularly limited, and any protein or raw material containing any protein can be used, as long as the hydrolyzate thereof contains the glycopeptide(s) or the peptide(s) represented by the general formula (a) or (b), or any one of Sequence formulas (I) to (IV). For example, any protein such as vegetable protein, animal protein, or protein derived from yeast can be used. Examples of the vegetable protein include seed proteins such as wheat protein, soybean protein, corn protein, and the like. Among them, wheat protein is particularly suitable in terms of the abundance ratio of amino acids.

As an enzyme to be used for the hydrolysis of the protein according to the present invention, a commercially available enzyme preparation as well as a naturally-derived enzyme which has been metabolized using a microorganism or the like can be used as long as it can enzymatically decompose a protein as the raw material or the starting raw material containing the protein. These enzymes may be used alone or in combination of two or more thereof.

As for the pH and the reaction temperature used at the time when any protein or a starting raw material containing the protein is subjected to an enzymatic hydrolysis treatment, the optimum conditions for the enzyme to be used or conditions close thereto may be appropriately employed. The pH can be adjusted by adding an acid or an alkali which is acceptable for foods and drinks.

The treatment time that the protein or the starting raw material containing the protein should be subjected to the enzymatic hydrolysis varies depending on the conditions relating to the decomposition, such as the kind of enzyme to be used for the hydrolysis of the protein, the amount of the enzyme to be used, the temperature, the pH, and the like. It is, however, preferably 20 to 100 hours. If the treatment time is much longer than necessary, there is a case that decomposition and browning unnecessarily occur, which may have an adverse influence on the quality of the hydrolyzate. Those skilled in the art can easily determine the preferred conditions for the hydrolysis treatment of a protein to obtain the glycopeptide or the peptide represented by any one of Sequence formulas (I) to (VI) by sampling the hydrolyzate from time to time during the hydrolysis treatment and then carrying out analysis.

The seasoning containing the glycopeptide(s) and/or the peptide(s) of the present invention can be obtained by collecting the liquid part of the raw material containing the enzymatically hydrolyzed protein by the use of ordinary procedures such as filtration, centrifugal separation, or the like. Such a seasoning may be subjected to a decolorizing treatment using activated carbon, an ultrafilter, or the like, a separation and purification treatment using various chromatographic techniques or membrane separation using a permeable membrane, or the like, and a concentration treatment such as membrane concentration or vacuum concentration, or the like. The thus-treated seasoning may be used as a purified seasoning which has been subjected to decolorization, purification, concentration, and the like. In addition, it is possible to obtain a powdery seasoning having excellent storage stability without having added table salt or the like, by spray-drying, freeze-vacuum drying, or the like, such a seasoning containing the glycopeptide and/or the peptide of the present invention.

Further, in a case where it is necessary to obtain a glycopeptide and/or a peptide per se of the present invention, it can be isolated and purified by treating such above-mentioned hydrolyzate of a protein or a seasoning containing a glycopeptide and/or a peptide of the present invention, using known separation and purification procedures such as ultrafiltration, reverse osmosis, dialysis, normal phase HPLC, reversed phase HPLC, ion-exchange chromatography, gel filtration chromatography, affinity chromatography, and the like.

The seasoning containing a glycopeptide and/or a peptide of the present invention can impart not only a kokumi taste but also the tightness of aftertaste, ripe feeling, and the like, to foods and drinks when added thereto, and has the effect of improving the taste of the whole of a food or a drink without particularly adding a flavor-enhancing seasoning (an umami seasoning).

There are a variety of foods such as soups, processed foods and the like, in respect of which the taste improving effect of a glycopeptide and/or a peptide of the present invention, such as impartment of a kokumi taste, can be provided, and in particular, the effect can be conspicuously provided in respect of fermented seasonings or fermented foods. That is, the glycopeptide and/or the peptide of the present invention exhibits conspicuously the effect on fermented seasonings or fermented foods such as soy sauce, soybean paste, cheese, and the like, and foods and drinks made therefrom, and can impart taste improving effects such as impartment of a kokumi taste, e.g., thickness, spread, unity, and the like, as well as improvement of the tightness of aftertaste, to these foods.

The state of the glycopeptide and/or the peptide of the present invention at the time when they are added to foods is not limited, and they may be in a dry powder state, a paste state, a liquid state, or the like. Further, since the glycopeptide and/or the peptide exhibits a kokumi taste imparting function as long as they are added to foods or drinks in such that the concentration thereof therein would be in the range of 1 ppb to 1,000 ppm by weight, preferably 1 ppb to 100 ppm by weight, upon eating, the glycopeptide and/or the peptide can, at any time, be added to foods or seasonings to realize the kokumi taste imparting effect. For example, the glycopeptide and/or the peptide can be added to a raw material before production or during production, or to a finished product after completion, or to a finished product at just before upon eating, during eating, or the like.

In general formula (a), each of A and B may independently be an amino acid residue derived from an amino acid selected from the group consisting of alanine, arginine, asparagines, aspartic acid, cysteine, glutamine, glutamic acid, glycine, histidine, isoleucine, leucine, lysine, methionine, phenylalanine, praline, serine, threonine, tryptophan, tyrosine, and valine. In a preferred embodiment, A is the amino acid residue derived from valine. In another preferred embodiment, B is the amino acid residue derived from threonine. In a particularly preferred embodiment, A is the amino acid residue derived from valine, and B is the amino acid residue derived from threonine.

Other features of the invention will become apparent in the course of the following descriptions of exemplary embodiments which are given for illustration of the invention and are not intended to be limiting thereof.

EXAMPLES

Example 1

Fractionation of Glycopeptide, Synthesis of Peptide, and Kokumi taste Imparting Function 500 g of wheat gluten "SWP-5A" (manufactured by Amylum) was added to, and sufficiently dispersed in, 2 L of water, and the resulting mixture was sterilized by heating at 120° C. for 20 minutes, whereby a dispersion liquid of wheat gluten was prepared. On the other hand, 30 g of soybean protein "ESUSAN PROTEN F" (manufactured by Ajinomoto Oil Mills, Inc.) was added to, and dispersed in, 2 L of water, and the resulting mixture was sterilized by heating at 120° C. for 20 minutes, whereby a dispersion liquid of defatted soybean was prepared. To this dispersion liquid of defatted soybean, an *Aspergillus oryzae* pre-cultured in a culture medium was added in such an amount that it would be present in an amount of 1% (v/v), and the mixture was subjected to culturing in a fermenter jar at 30° C. for 36 hours. 0.6 L of the *Aspergillus oryzae*-cultured broth was added to 2 L of the dispersion liquid of wheat gluten, and the resulting mixture was subjected to hydrolysis reaction in a fermenter jar at 36° C. for 72 hours, while being agitated with aeration. The thus-obtained hydrolyzate was subjected to solid-liquid separation using a Nutsche funnel to obtain a filtrate. To the filtrate was then added 60 g of activated carbon. The resulting mixture was heated at 60° C. for 10 minutes to decolorize the filtrate. The activated carbon was removed from the obtained decolorized liquid with a Nutsche funnel, and the filtrate was dried with a lyophilizer to obtain powdery, enzymatically decomposed wheat gluten seasoning.

The thus-obtained powdery, enzymatically-decomposed wheat gluten seasoning was dissolved in water, and the resulting aqueous solution was fractionated using an ultrafilter membrane "Prep/Scale-TFF PLAC 1K" (manufactured by MILLIPORE Corporation). The obtained fraction of a molecular weight of 1,000 or higher was further fractionated with the use of a gel filtration "Superdex 75 pg26/60" (manufactured by Amersham Biosciences) to obtain a fraction in respect of which an absorption of 280 nm was confirmed with a UV detector. This fraction was fractionated into Nos. 1 to 12 fractions by reversed phase HPLC (Capcellpack C-18 UG, manufactured by Shiseido Co., Ltd.). For the fractionation, two solvents A and B were used. Solvent A was a 0.05% by volume trifluoroacetic acid (TFA) aqueous solution, and Solvent B was a 0.05% by volume TFA 50% by volume acetonitrile aqueous solution. The column was equilibrated with Solvent A. After injecting a sample, the proportion of Solvent B was increased linearly to 100% in 50 min.

2 g of a commercially available chicken consommé soup (manufactured by Ajinomoto Co., Inc.) was added to 100 mL of water to prepare a chicken consommé soup, and then each of the fractions was added to the chicken consommé soup. The resulting mixtures were subjected to organoleptic evaluation, to confirm that there were two fractions which had a particularly strong effect of improving taste. These two fractions were each again fractionated by reversed phase HPLC ("Carbon-500" manufactured by Tosoh Corporation). The following conditions were used to obtain two peaks at 44.8 minutes and 46.6 minutes. For the fractionation, two solvents A and B were used. Solvent A was a 0.05% by volume trifluoroacetic acid (TFA) aqueous solution, and Solvent B was a 0.05% by volume TFA 50% by volume acetonitrile aqueous solution. The column was equilibrated with Solvent A. After injecting a sample, the proportion of Solvent B was increased linearly to 100% in 167 min. The fractionated two peaks were analyzed with an LC-MS/MS (liquid chromatography-tandem mass spectrometry), to confirm that the former peak had fragments, that is, $[M+H]^+=m/z$ 1640, 1494, 1478, 1362, 1332, 1316, 1200, 1184, 1038, 876, 819, 673, and 470, and that the latter peak had fragments, that is, $[M+H]^+=m/z$ 1478, 1346, 1332, 1316, 1200, 1184, 1038, 876, 819, 673, and 470. Further, the former and latter peaks were analyzed by some known methods of analysis such as NMR, a peptide sequencer, an enzymatic decomposition treatment, and the like (R.Takahashi, "Biochemical Experiment Methods 23: Method for Studying Glycoprotein Sugar Chain," published by Gakkai Shuppan Center, 1989), to confirm that the peaks were due to the glycopeptides having the structures represented by Sequence formulas (I) (SEQ ID NO: 1) and (II) (SEQ ID NO: 1), respectively.

In these two glycopeptides, common peptide moieties (Sequence formulas (III) (SEQ IID NO: 1), (IV), (V) and (VI) existed. Therefore, in order to confirm the taste improving function of the peptides, those peptides represented by Sequence formulas (III) (SEQ ID NO: 1), (IV), (V) and (VI) were obtained by synthesis using a "433A Peptide Synthesizer" (manufactured by Applied Biosystems), followed by purifying by reversed phase HPLC ("Carbon-500", manufactured by Tosoh Corporation). For fractionation, two solvents A and B were used. Solvent A was a 0.05% by volume trifluoroacetic acid (TFA) aqueous solution, and Solvent B was a 0.05% by volume TFA 50% by volume acetonitrile aqueous solution. The column was equilibrated with Solvent A. After injecting a sample, the proportion of Solvent B was increased linearly to 100% in 167 mm.

In order to confirm the kokumi taste imparting function and the threshold value of the glycopeptides and the peptide represented by Sequence formulas (I) to (III) (SEQ ID NO: 1) (hereinafter, the glycopeptides and the peptide represented by Sequence formulas (I) to (III) may also be referred to as Glycopeptide I, Glycopeptide II, and Peptide III, respectively), Glycopeptide I and Glycopeptide II were each added to a chicken consommé soup in such that the concentration thereof would be 0.1 ppb to 1.0 ppm by weight upon eating, and Peptide III was added to the chicken consommé soup in such that the concentration thereof would be 0.1 ppb to 100 ppm by weight upon eating. As a control, a non-added chicken consommé soup was prepared. For each of the three glycopeptides and peptide, organoleptic evaluation was carried out by 16 taste panelists according to a paired comparison test (the panelists should choose one with a stronger kokumi taste). The results are shown in the following Table 1. In the above organoleptic evaluation, there was a significant difference in the effect caused by adding Glycopeptide I or II or Peptide III in the case where the concentration thereof was 1 ppb by weight or more upon eating. Therefore, the lower limit of the threshold value was set to 1 ppb by weight.

TABLE 1

Evaluation of chicken consommé soup (n = 16)

| Amount added | Comparative organoleptic evaluation test A | | Comparative organoleptic evaluation test B | | Comparative organoleptic evaluation test C | |
| --- | --- | --- | --- | --- | --- | --- |
| | Non-added | Glyco-peptide I | Non-added | Glyco-peptide II | Non-added | Peptide III |
| 0.1 ppb | 4 | 12 | 5 | 11 | 7 | 9 |
| 1.0 ppb | 2 | 14** | 2 | 14** | 3 | 13* |
| 10 ppb | 0 | 16*** | 0 | 16*** | 2 | 14** |
| 1.0 ppm | 0 | 16*** | 0 | 16*** | 0 | 16*** |
| 100 ppm | — | — | — | — | 0 | 16*** |

***Significance level of 0.1%;
**Significance level of 1%; and
*Significance level of 5%.

Example 2

Taste Improving Function of Glycopeptides and Peptide

In order to verify a taste improving function for solutions having five basic tastes, Glycopeptide I, Glycopeptide II, and Peptide III were respectively added in an amount of 100 ppb by weight to a 0.45% by weight sodium glutamate aqueous solution, a 0.05% by weight sodium inosinate aqueous solution, a 0.06% by weight sodium dl-tartarate aqueous solution, a 2.4% by weight saccharose aqueous solution, a 0.9% by weight sodium chloride aqueous solution, and a 0.1% by weight caffeine aqueous solution. Each resulting solution was subjected to organoleptic evaluation using non-added aqueous solutions as the controls in the same manner as in the organoleptic evaluation of Example 1. As a result, it was found that all the three glycopeptides and peptide had the effect of improving sweet taste and sour taste, and that the two glycopeptides enhanced bitter taste.

Example 3

Taste Improving Function for "Mentsuyu"

In order to verify a taste improving function for "Mentsuyu" (a soup for Japanese noodle) in the same manner as in the organoleptic evaluation of Example 1, the three glycopeptides and peptide were each added in an amount of 1 ppb by weight to Mentsuyu prepared according to the formulation shown in the following Table 2. Each resulting solution was subjected to organoleptic evaluation by 16 taste panelists according to a paired comparison test, using non-added Mentsuyu as the control. The results are shown in the following Table 3.

TABLE 2

Formulation of "Mentsuyu"

| Materials | Composition (wt. %) |
|---|---|
| Soy sauce | 15.0 |
| Sugar | 6.0 |
| Soup stock of dried bonito (manufactured by Ajinomoto Co., Inc. under the product name of "Ichibandashi-katsuodashi") | 4.0 |
| Table Salt | 1.5 |
| Water | 73.5 |
| Total | 100.0 |

Soy sauce, sugar, soup stock, and table salt were mixed with, and dissolved in water, and the resulting mixture was heated at 85° C. for 1 hour.

TABLE 3

Evaluation of "Mentsuyu" (n = 16)

| | Comparative organoleptic evaluation test A | | Comparative organoleptic evaluation test B | | Comparative organoleptic evaluation test C | |
|---|---|---|---|---|---|---|
| | Non-added | Glyco-peptide I | Non-added | Glyco-peptide II | Non-added | Peptide III |
| Stronger "kokumi" taste | 1 | 15*** | 1 | 15*** | 3 | 13* |
| Comments | Lack of Unity | Taste became thick | Lack of Unity | Taste was Spread | Lack of Unity | Taste was Spread |

***Significance level of 0.1%;
**Significance level of 1%; and
*Significance level of 5%.

Example 4

Taste Improving Function for Cheese Sauce

In order to verify a taste improving function for cheese sauce, the three glycopeptides and peptide were each added in an amount of 1 ppm by weight to a cheese sauce prepared according to the formulation shown in the following Table 4, and then an organoleptic evaluation was performed in the same manner as in Example 1. Each of the sauces added with one of the three glycopeptides and peptide was subjected to organoleptic evaluation by 14 taste panelists according to a paired comparison test, using non-added cheese sauce as the control. The results are shown in the following Table 5.

TABLE 4

Formulation of cheese sauce

| Materials | Composition (wt. %) |
|---|---|
| Cheese | 50.0 |
| Potato starch | 2.0 |
| Wheat flour | 0.5 |
| Water | 47.5 |
| Total | 100.0 |

Heat-stirred until creamy, and then used.

TABLE 5

Evaluation of cheese sauce (n = 14)

| | Comparative organoleptic evaluation test A | | Comparative organoleptic evaluation test B | | Comparative organoleptic evaluation test C | |
|---|---|---|---|---|---|---|
| | Non-added | Glyco-peptide I | Non-added | Glyco-peptide II | Non-added | Peptide III |
| Stronger "kokumi" taste | 0 | 14*** | 2 | 12* | 2 | 12* |
| Comments | — | Aftertaste lasted | — | Taste was Expanded | — | Taste was Expanded |

***Significance level of 0.1%;
**Significance level of 1%; and
*Significance level of 5%.

Example 5

Taste Improving Function for Beef Extract

In order to verify a taste improving function for a commercially available beef extract (manufactured by Bordon), the three glycopeptides and peptide were each added in an amount of 10 ppb by weight to a beef extract solution formulated according to the mixing ratio shown in the following Table 6, and then an organoleptic evaluation was performed in the same manner as in Example 1. Each resulting solution was subjected to organoleptic evaluation by 16 taste panelists according to a paired comparison test, using the non-added beef extract solution as the control. The results are shown in the following Table 7.

TABLE 6

Formulation of beef extract solution

| Materials | Composition (wt. %) |
|---|---|
| Beef extract (manufactured by Bordon) | 2.0 |
| Table salt | 0.2 |
| Hot water | 97.8 |
| Total | 100.0 |

Stir-dissolved, and then used.

TABLE 7

Evaluation of beef extract solution (n = 16)

| | Comparative organoleptic evaluation test A | | Comparative organoleptic evaluation test B | | Comparative organoleptic evaluation test C | |
|---|---|---|---|---|---|---|
| | Non-added | Glyco-peptide I | Non-added | Glyco-peptide II | Non-added | Peptide III |
| Stronger "kokumi" taste | 1 | 15*** | 3 | 13* | 3 | 13* |
| Comments | Lack of Thickness | Tightened in aftertaste | Lack of Thickness | Taste was Spread | Lack of Thickness | Taste was Spread |

***Significance level of 0.1%;
**Significance level of 1%; and
*Significance level of 5%.

Example 6

Taste Improving Function for "Mentsuyu"

In order to verify the taste improving function of a liquid comprising enzymatically decomposed wheat gluten, that is, a seasoning containing the three glycopeptides and peptide, for Mentsuyu, the seasoning comprising enzymatically decomposed wheat gluten (that is, the decolorized liquid of Example 1 from which the activated carbon had been removed) was added in an amount of 0.1% by volume to Mentsuyu prepared according to the formulation shown in Table 2, and then an organoleptic evaluation was performed in the same manner as in Example 1. Organoleptic evaluation was carried out by 20 taste panelists according to a paired comparison test, using the non-added Mentsuyu as the control. The results are shown in the following Table 8.

TABLE 8

Evaluation of "mentsuyu" (n = 20)

| | Comparative organoleptic evaluation test | |
|---|---|---|
| | Non-added | Enzymatically decomposed wheat gluten liquid, added |
| Stronger "kokumi" taste | 0 | 20*** |
| Comments | Lack of unity | Became thick, Unity provided |

***Significance level of 0.1%;
**: Significance level of 1%; and
*: Significance level of 5%.

Example 7

Taste Improving Function for Cheese Sauce

In order to verify the taste improving function of the liquid comprising enzymatically decomposed wheat gluten, that is, a seasoning containing the three glycopeptides and peptide, for cheese sauce, the seasoning comprising enzymatically decomposed wheat gluten (that is, the powdered seasoning of Example 1 formed from the decolorized liquid from which the activated carbon had been removed) was added in an amount of 0.05% by weight to a cheese sauce prepared according to the formulation shown in Table 4, and then an organoleptic evaluation was performed in the same manner as in Example 1. Organoleptic evaluation was carried out by 20 taste panelists according to a paired comparison test, using the non-added cheese sauce as the control. The results are shown in the following Table 9.

TABLE 9

Evaluation of cheese sauce (n = 20)

| | Comparative organoleptic evaluation test | |
|---|---|---|
| | Non-added | Enzymatically decomposed wheat gluten liquid, added. |
| Stronger "kokumi" taste | 0 | 20*** |
| Comments | — | Taste was expanded Titer was strengthen |

(***Significance level of 0.1%,
**: Significance level of 1%,
*: Significance level of 5%)

Example 8

Taste Improving Function for Beef Extract

In order to verify the taste improving function of a liquid comprising enzymatically decomposed wheat gluten, that is, a seasoning containing the three glycopeptides and peptide, for a commercially available beef extract, the seasoning comprising enzymatically decomposed wheat gluten (that is, the powdered seasoning of Example 1 formed from the decolorized liquid from which the activated carbon had been removed) was added in an amount of 0.01% by weight to a beef extract solution formulated according to the mixing ratio shown in Table 6, and then an organoleptic evaluation was performed in the same manner as in Example 1. Organoleptic evaluation was carried out by 16 taste panelists according to a paired comparison test, using the non-added beef extract solution as a control. The results are shown in the following Table 10.

TABLE 10

Evaluation of beef extract solution (n = 16)

| | Comparative organoleptic evaluation test | |
|---|---|---|
| | Non-added | Enzymatically decomposed wheat gluten liquid, added |
| Stronger "kokumi" taste | 2 | 14** |
| Comments | Thickness-Less | Taste was spread. Continuity was provided |

***: Significance level of 0.1%;
**Significance level of 1%; and
*: Significance level of 5%.

Example 9

Taste Improving Function for Tomato Soup

In order to verify the taste improving function of a liquid comprising enzymatically decomposed wheat gluten, that is, a seasoning containing the three glycopeptides and peptide, for a tomato soup in the same manner, the seasoning comprising enzymatically decomposed wheat gluten (that is, the powdered seasoning of Example 1 formed from the decolorized liquid from which the activated carbon had been removed) was added in an amount of 0.05% by weight to a tomato soup prepared according to the formulation shown in the following Table 11, and then an organoleptic evaluation was performed in the same manner as in Example 1. Organoleptic evaluation was carried out by 16 taste panelists according to a paired comparison test, using the non-added tomato soup as the control. The results are shown in the following Table 12.

TABLE 11

Formulation of Tomato soup

| Materials | Composition (wt. %) |
|---|---|
| Tomato juice | 60.00 |
| Sugar | 1.80 |
| Skimmed milk | 1.70 |
| Potato starch | 1.60 |
| Table salt | 0.60 |
| MSG | 0.30 |
| Yeast extract | 0.20 |
| Onion powder | 0.17 |
| Garlic powder | 0.01 |
| Paprika powder | 0.01 |
| Carrot powder | 0.01 |
| water | 33.60 |
| Total | 100.00 |

Dissolved and heat-stirred, and then used.

TABLE 12

Evaluation of Tomato soup (n = 16)

| | Comparative organoleptic evaluation test | |
|---|---|---|
| | Non-added | Enzymatically decomposed wheat gluten liquid, added |
| Stronger "kokumi" taste | 1 | 15*** |
| Comments | — | Unity and ripe feeling were increased |

***Significance level of 0.1%;
**: Significance level of 1%; and
*: Significance level of 5%.

Example 10

Taste Improving Function for Soybean Paste

In order to verify the taste improving function of a seasoning comprising enzymatically decomposed wheat gluten, that is, a seasoning containing the three glycopeptides and peptide, for soybean paste, the seasoning comprising enzymatically decomposed wheat gluten (that is, a powdered seasoning of Example 1 formed from the decolorized liquid from which the activated carbon had been removed) was added in an amount of 0.05% by weight to a soybean paste-flavored soup for Chinese noodle prepared according to the formulation shown in the following Table 13, and then an organoleptic evaluation was performed in the same manner as in Example 1. Organoleptic evaluation was carried out by 13 taste panelists according to a paired comparison test, using the non-added soybean paste-flavored soup for Chinese noodle as the control. The results are shown in the following Table 14.

TABLE 13

Formulation of hot aqueous soybean paste solution

| Materials | Composition (wt. %) |
|---|---|
| Soybean paste | 20.00 |
| Soy sauce | 1.50 |
| Sugar | 3.00 |
| Table salt | 0.80 |
| MSG | 2.20 |
| Nucleic acid (IN) | 0.04 |
| Chicken extract | 0.90 |
| Pork extract | 1.30 |
| Garlic paste | 0.89 |
| Ginger paste | 0.20 |
| White pepper | 0.05 |
| Capsicum powder | 0.05 |
| Lard | 4.40 |
| Vegetable oil (sesame) | 1.30 |
| Hot water | 63.36 |
| Total | 100.0 |

Used after stir-dissolved.

TABLE 14

Evaluation of hot aqueous soybean paste solution (n = 13)

| | Comparative organoleptic evaluation test | |
|---|---|---|
| | Non-added | Enzymatically decomposed wheat gluten liquid, added |
| Stronger "kokumi" taste | 0 | 13*** |
| Comments | — | Unity and ripe feeling were provided |

***Significance level of 0.1%;
**: Significance level of 1%; and
*: Significance level of 5%.

Example 11

Taste Improving Function for Beef Extract

In order to verify a taste improving function for a commercially available beef extract (manufactured by Bordon) in the same manner as in the organoleptic evaluation of Example 1, the glycopeptides and peptides listed in the following Table 15, were each added in an amount of 10 ppb, 1 ppm, or 100 ppm by weight to beef extract solutions formulated according to the mixing ratio shown in Table 6 above. Each resulting solution was subjected to organoleptic evaluation by 14 taste panelists according to a paired comparison test, using the non-added beef extract solution as the control. The results are also shown in the following Table 15.

Incidentally, in the Table 15 indicating the results, Marks Δ, O, and OO represent "Equal or inferior in the kokumi taste to the control," "Stronger in the kokumi taste than the control," and "Remarkably stronger in the kokumi taste than the control", respectively.

TABLE 15

Evaluation of beef extract

| Samples | 10 ppb | 1 ppm | 100 ppm |
|---|---|---|---|
| Glycopeptide I | ⊙⊙ | ⊙⊙ | ⊙⊙ |
| Peptide III (Val-Asn-His-Thr) | ⊙⊙ | ⊙⊙ | ⊙⊙ |
| Val-Asn-His | ○ | ⊙⊙ | ⊙⊙ |
| Asn-His-Thr | ○ | ⊙⊙ | ⊙⊙ |
| Val-Asn | Δ | Δ | Δ |
| Asn-His | ○ | ○ | ⊙⊙ |
| Val-Gln | Δ | Δ | Δ |
| His-Ser | Δ | Δ | Δ |

INDUSTRIAL APPLICABILITY

According to the present invention, it is possible to provide a glycopeptide and/or a peptide which has the function of imparting a kokumi taste to foods when added thereto. Further, according to the present invention, it is possible to provide a seasoning containing such a glycopeptide and/or peptide, which has a strong effect of improving taste such as the function of imparting the kokumi taste to foods. Furthermore, according to the present invention, it is possible to impart a kokumi taste to a food and improve the taste of foods by directly adding such a glycopeptide and/or peptide to foods or by adding a seasoning which contains such a glycopeptide and/or peptide to a food.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A glycopeptide or peptide having the chemical structure represented by the following general formula (b) (SEQ ID NO: 1):

General formula (b)

wherein Val, Asn, His and Thr represent a valine residue, an asparagine residue, a histidine residue, and a threonine residue, respectively, and X represents a hydrogen atom or a sugar chain.

2. A method of preparing a food or seasoning with a kokumi taste, comprising:
   adding at least one glycopeptide or peptide according to claim 1 to the food or seasoning in an amount such that the at least one glycopeptide or peptide is present in the food or seasoning in an amount of 1 ppb to 1,000 ppm (w/w), based on a total weight of the at least one glycopeptide or peptide and the food or seasoning.

3. A method of preparing a food with a kokumi taste, comprising:
   adding a seasoning to the foods;
   wherein:
   the seasoning comprises at least one glycopeptide or peptide according to claim 1;
   the at least one glycopeptide or peptide is present in the seasoning in an amount of 1 ppb to 1,000 ppm (w/w), based on a total weight of the seasoning and the at least one glycopeptide or peptide; and
   the seasoning is added to the food in an amount such that the seasoning is present in the food in an amount of 0.01-10% (w/w) based on a total weight of the seasoning and the food.

---

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptied
<220> FEATURE:
<221> NAME/KEY: MOD_RES
<222> LOCATION: (2)..(2)
<223> OTHER INFORMATION: The Asn at position 2 may be unmodified or
      modified with a sugarchain

<400> SEQUENCE: 1

Val Asn His Thr
1
```

4. A glycopeptide or peptide, which has a chemical structure represented by the following formula (I) (SEQ ID NO: 1), (II) (SEQ ID NO: 1) or (III) (SEQ ID NO: 1):

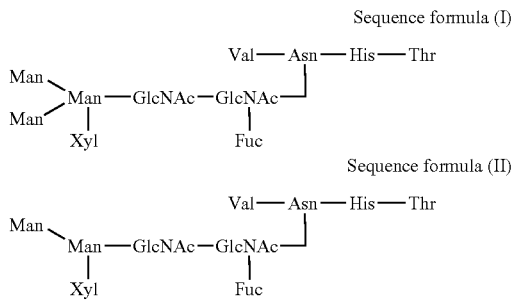

| Sequence formula (III) | Sequence formula (IV) | Sequence formula (V) | Sequence formula (VI) |
|---|---|---|---|
| Val-Asn-His-Thr | Val-Asn-His | Asn-His-Thr | Asn-His | wherein Val, Asn, His, and Thr represent a valine residue, an asparagine residue, a histidine residue, and a threonine residue, respectively, and GlcNAc represents an N-acetyl-glucosamine residue, Fuc represents a fucose residue, Man represents a mannose residue, and Xyl represents a xylose residue.

5. A method of preparing a food or seasoning with a kokumi taste, comprising:
adding at least one glycopeptide or peptide according to claim 4 to the food or seasoning in an amount such that the at least one glycopeptide or peptide is present in an amount of 1 ppb to 1,000 ppm (w/w), based on a total weight of the at least one glycopeptide or peptide and the food or seasoning.

6. A method of preparing a food with a kokumi taste, comprising:
adding a seasoning to the food;
wherein:
the seasoning comprises at least one glycopeptide or peptide according to claim 4;
the at least one glycopeptide or peptide is present in the seasoning in an amount of 1 ppb to 1,000 ppm (w/w), based on a total weight of the seasoning and the at least one glycopeptide or peptide; and
the seasoning is added to the food in an amount such that the seasoning is present in the food in an amount of 0.01-10% (w/w), based on a total weight of the seasoning and the food.

7. A food or seasoning, prepared by the method of claim 2.
8. A food, prepared by the method of claim 3.
9. A food or seasoning, prepared by the method of claim 5.
10. A food, prepared by the method of claim 6.
11. An isolated or purified glycopeptide or peptide having the chemical structure represented by the following general formula (b) (SEQ ID NO: 1):

General formula (b)

wherein Val, Asn, His and Thr represent a valine residue, an asparagine residue, a histidine residue, and a threonine residue, respectively, and X represents a hydrogen atom or a sugar chain.

12. An isolated or purified glycopeptide or peptide, which has a chemical structure represented by the following formula (I) (SEQ ID NO: 1), (II) (SEQ ID NO: 1) or (III) (SEQ ID NO: 1):

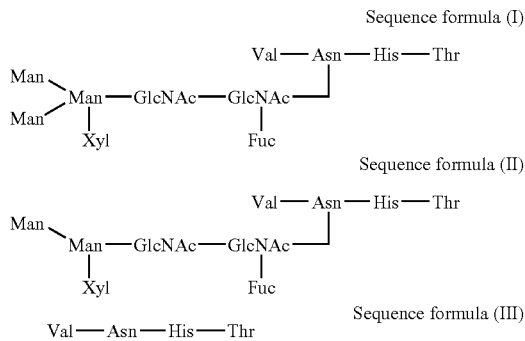

wherein Val, Asn, His, and Thr represent a valine residue, an asparagine residue, a histidine residue, and a threonine residue, respectively, and GlcNAc represents an N-acetyl-glucosamine residue, Fuc represents a fucose residue, Man represents a mannose residue, and Xyl represents a xylose residue.

* * * * *